United States Patent
Jacobson et al.

(10) Patent No.: US 12,233,066 B2
(45) Date of Patent: Feb. 25, 2025

(54) COMBINATIONS OF INHIBITORS OF INFLUENZA VIRUS REPLICATION

(71) Applicant: COCRYSTAL PHARMA, INC., Bothell, WA (US)

(72) Inventors: Irina C. Jacobson, Sammamish, WA (US); Biing Yuan Lin, Bellevue, WA (US); Sam S K Lee, Edmonds, WA (US)

(73) Assignee: COCRYSTAL PHARMA, INC., Bothell, WA (US)

( * ) Notice: Subject to any disclaimer, the term of this patent is extended or adjusted under 35 U.S.C. 154(b) by 983 days.

(21) Appl. No.: 17/286,026

(22) PCT Filed: Oct. 17, 2019

(86) PCT No.: PCT/US2019/056632
§ 371 (c)(1),
(2) Date: Apr. 16, 2021

(87) PCT Pub. No.: WO2020/081751
PCT Pub. Date: Apr. 23, 2020

(65) Prior Publication Data
US 2021/0353629 A1 Nov. 18, 2021

Related U.S. Application Data

(60) Provisional application No. 62/746,884, filed on Oct. 17, 2018.

(51) Int. Cl.
*A61K 31/519* (2006.01)
*A61K 39/145* (2006.01)
*A61K 45/06* (2006.01)

(52) U.S. Cl.
CPC .......... *A61K 31/519* (2013.01); *A61K 39/145* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,079,038 A | 3/1978 | Choi et al. | |
| 4,093,709 A | 6/1978 | Choi et al. | |
| 4,131,648 A | 12/1978 | Choi et al. | |
| 4,138,344 A | 2/1979 | Choi et al. | |
| 4,180,646 A | 12/1979 | Choi et al. | |
| 4,304,767 A | 12/1981 | Heller et al. | |
| 4,353,656 A | 10/1982 | Sohl et al. | |
| 4,501,729 A | 2/1985 | Boucher et al. | |
| 4,753,788 A | 6/1988 | Gamble | |
| 4,778,054 A | 10/1988 | Newell et al. | |
| 4,811,731 A | 3/1989 | Newell et al. | |
| 4,946,931 A | 8/1990 | Heller et al. | |
| 5,035,237 A | 7/1991 | Newell et al. | |
| 5,590,645 A | 1/1997 | Davies et al. | |
| 5,860,419 A | 1/1999 | Davies et al. | |
| 5,873,360 A | 2/1999 | Davies et al. | |
| 5,968,543 A | 10/1999 | Heller et al. | |
| 6,413,536 B1 | 7/2002 | Gibson et al. | |
| 6,596,296 B1 | 7/2003 | Nelson et al. | |
| 6,613,355 B2 | 9/2003 | Ng et al. | |
| 6,632,666 B2 | 10/2003 | Baust et al. | |
| 6,667,371 B2 | 12/2003 | Ng et al. | |
| 6,732,732 B2 | 5/2004 | Edwards et al. | |
| 6,749,835 B1 | 6/2004 | Lipp et al. | |
| 6,766,799 B2 | 7/2004 | Edwards et al. | |
| 6,848,197 B2 | 2/2005 | Chen et al. | |
| 6,956,021 B1 | 10/2005 | Edwards et al. | |
| 7,008,644 B2 | 3/2006 | Batycky et al. | |
| 7,032,593 B2 | 4/2006 | Johnston et al. | |
| 7,048,908 B2 | 5/2006 | Basu et al. | |
| 7,146,978 B2 | 12/2006 | Edwards et al. | |
| 7,182,961 B2 | 2/2007 | Batycky et al. | |
| 7,252,840 B1 | 8/2007 | Batycky et al. | |
| 7,279,182 B2 | 10/2007 | Lipp et al. | |
| 7,384,649 B2 | 6/2008 | Batycky et al. | |
| 7,678,364 B2 | 3/2010 | Edwards et al. | |
| 11,014,941 B2 * | 5/2021 | Jacobson | A61K 9/127 |
| 11,040,048 B2 | 6/2021 | Shishido et al. | |
| 11,098,042 B2 | 8/2021 | Ren et al. | |

FOREIGN PATENT DOCUMENTS

| | | |
|---|---|---|
| CN | 108276401 A | 7/2018 |
| EP | 69715 A1 | 1/1983 |
| EP | 0504263 B1 | 8/1997 |
| GB | 2064336 A | 6/1981 |
| GB | 2129691 A | 5/1984 |
| GB | 2169265 A | 7/1986 |
| GB | 2178965 A | 2/1987 |
| GB | 2242134 A | 9/1991 |

(Continued)

OTHER PUBLICATIONS

Chinese Patent Appliation No. 201980073306.0, Office Action and Search Report, dated Feb. 5, 2024.

Xiong et al., Design, synthesis and biological evaluation of novel, orally bioavailable pyrimidine-fused heterocycles as influenza PB2 inhibitors, European Journal of Medicinal Chemistry, 162:249-265 (2019).

Berge et al., Pharmaceutical Salts, J. Pharm. Sci., 66(1): 1-19 (Jan. 1977).

Byrn et al., Preclinical activity of VX-787, a first-in-class, orally bioavailable inhibitor of the influenza virus polymerase PB2 subunit, Antimicrob Agents Chemother., 59(3):1569-82 (2015).

(Continued)

*Primary Examiner* — Traviss C McIntosh, III
(74) *Attorney, Agent, or Firm* — MARSHALL, GERSTEIN & BORUN LLP

(57) ABSTRACT

Provided herein are combinations of compounds that can inhibit the replication of influenza viruses, reduce the amount of influenza viruses, and/or treat influenza.

20 Claims, 2 Drawing Sheets

(56) References Cited

FOREIGN PATENT DOCUMENTS

Figure 1:
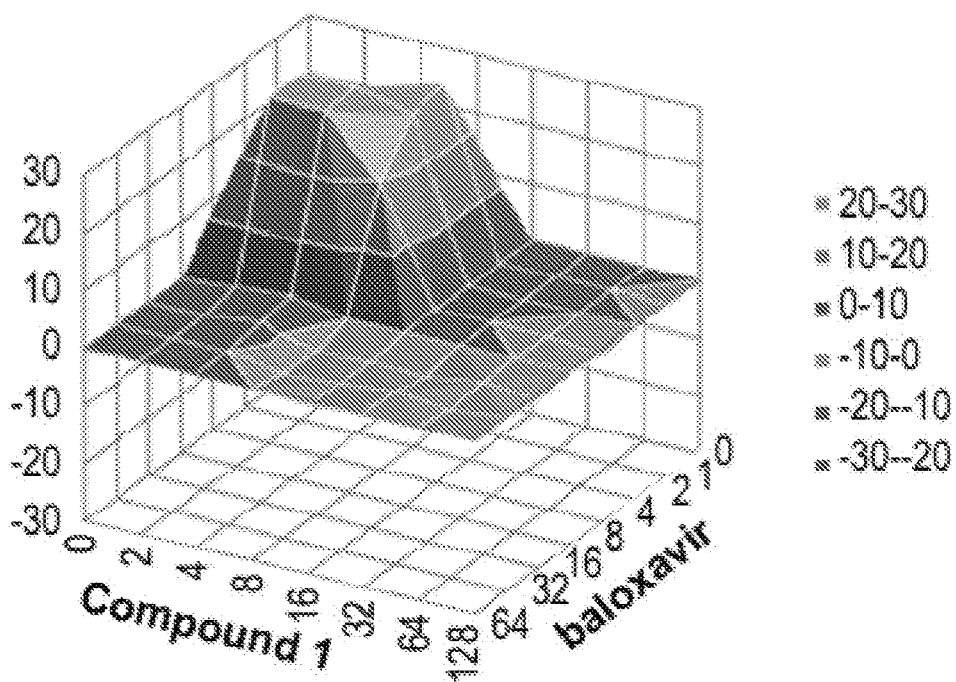

| WO | WO-2005/023335 A2 | 3/2005 |
| WO | WO-2017/104691 A1 | 6/2017 |
| WO | WO-2018/157830 A1 | 9/2018 |
| WO | WO-2018/200425 A1 | 11/2018 |

OTHER PUBLICATIONS

Chou et al., Quantitative analysis of dose-effect relationships: the combined effects of multiple drugs or enzyme inhibitors, Adv. Enzyme Regul., 22:27-55 (1984).
Holford et al., Understanding the dose-effect relationship: clinical application of pharmacokinetic-pharmacodynamic models, Clin. Pharmacokinet., 6(6):429-53 (Nov.-Dec. 1981).
International Application No. PCT/US2019/056632, International Search Report and Written Opinion, mailed Jan. 28, 2020.
Liu et al., A Small-Molecule Compound Has Anti-influenza A Virus Activity by Acting as a "PB2 Inhibitor", Mol. Pharm., 15(9):4110-4120 (2018).
Stelzmueller et al., Thoracic endovascular repair for acute complicated type B aortic dissections, J. Vasc. Surg., 69(2):318-26 (2019).
Willis et al., Therapeutic liposomal dry powder inhalation aerosols for targeted lung delivery, Lung, 190(3):251-62 (Jun. 2012).

\* cited by examiner

COMBINATIONS OF INHIBITORS OF INFLUENZA VIRUS REPLICATION

FIELD

This disclosure relates generally to combinations of inhibitors of influenza virus replication, and methods of treating or preventing an influenza infection or replication by administering the combinations to a patient in need of treatment thereof.

BACKGROUND

Influenza spreads around the world in seasonal epidemics, resulting in the deaths of hundreds of thousands of people annually-millions in pandemic years. For example, three influenza pandemics occurred in the 20th century and killed tens of millions of people, with each of these pandemics being caused by the appearance of a new strain of the virus in humans. Often, these new strains result from the spread of an existing influenza virus to humans from other animal species.

Influenza is primarily transmitted from person to person via large virus-laden droplets that are generated when infected persons cough or sneeze; these large droplets can then settle on the mucosal surfaces of the upper respiratory tracts of susceptible individuals who are near (within about 6 feet) to infected persons. Transmission might also occur through direct contact or indirect contact with respiratory secretions, such as touching surfaces contaminated with influenza virus and then touching the eyes, nose or mouth. Adults might be able to spread influenza to others from 1 day before getting symptoms to approximately 5 days after symptoms start. Young children and persons with weakened immune systems might be infectious for 10 or more days after onset of symptoms.

Influenza viruses are RNA viruses of the family Orthomyxoviridae, which comprises five genera: Influenza virus A, Influenza virus B, Influenza virus C, Isavirus and Thogotovirus.

The Influenza virus A genus is responsible for seasonal flu and pandemic flu epidemics. It has one species, influenza A virus, and wild aquatic birds are the natural hosts for a large variety of influenza A. Occasionally, viruses are transmitted to other species and may then cause devastating outbreaks in domestic poultry or give rise to human influenza pandemics. The type A viruses are the most virulent human pathogens among the three influenza types and cause the most severe disease. The influenza A virus can be subdivided into different serotypes based on the antibody response to these viruses. The serotypes that have been confirmed in humans, ordered by the number of known human pandemic deaths, are: H1N1 (which caused Spanish influenza in 1918), H2N2 (which caused Asian Influenza in 1957), H3N2 (which caused Hong Kong Flu in 1968), H5N1 (a pandemic threat in the 2007-08 influenza season), H7N7 (which is a potential pandemic threat, H1N2 (endemic in humans and pigs), H9N2, H7N2, H7N3 and H10N7.

The Influenza virus B genus is responsible for seasonal flu, and has one species, influenza B virus. Influenza B almost exclusively infects humans and is less common than influenza A. The only other animal known to be susceptible to influenza B infection is the seal. This type of influenza mutates at a rate 2-3 times slower than type A and consequently is less genetically diverse, with only one influenza B serotype. Because of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

The Influenza virus C genus has one species, influenza C virus, which infects humans and pigs and can cause severe illness and local epidemics. However, influenza C is less common than the other types and usually seems to cause mild disease in children.

Influenza viruses are very similar in structure across serotypes and genera. The influenza virus genome consists of eight single-stranded RNAs packed into rod-like structures of varying size, known as the ribonucleoprotein complex (RNP). Each RNP contains a unique viral RNA, multiple copies of the scaffolding nucleoprotein, and a heterotrimeric viral polymerase consisting of the PA, PB1, and PB2 subunits, which catalyzes the transcription and replication of the viral genome. Recent biochemical and structural studies of influenza polymerase complex provide insight into the mechanistic understanding of cap-snatching and RNA synthesis by influenza polymerase. Briefly, the PB2 cap-binding domain first sequesters the host pre-mRNAs by binding to their 5' cap. PA, the endonuclease subunit, then cleaves the captured pre-mRNA 10-13 nucleotides downstream of the cap. The PB2 subunit subsequently rotates about 700 to direct the capped primer into the PB1 polymerase active site. The PB1 subunit directly interacts with both PB2 and PA subunits. These subunits contain highly conserved domains among different influenza strains, and have attracted as an attractive anti-influenza drug target. In addition to the polymerase complex, the influenza genome encodes its own neuraminidase (NA), hemagglutinin (HA), nucleoprotein (NP), matrix proteins, M1 and M2, and non-structural proteins, NS1 and NS2. NA is the target for the antiviral drugs oseltamivir (Tamiflu®), laninamivir (Inavir®), peramivir, and zanamivir (Relenza®). These drugs inhibit the enzymatic activity of NA, thus slowing down the release of progeny virus from infected cells.

Influenza produces direct costs due to lost productivity and associated medical treatment, as well as indirect costs of preventative measures. In the United States, influenza is responsible for a total cost of over $10 billion per year, while it has been estimated that a future pandemic could cause hundreds of billions of dollars in direct and indirect costs. Preventative costs are also high. Governments worldwide have spent billions of U.S. dollars preparing and planning for a potential H5N1 avian influenza pandemic, with costs associated with purchasing drugs and vaccines as well as developing disaster drills and strategies for improved border controls.

Current treatment options for influenza include vaccination, and chemotherapy or chemoprophylaxis with anti-viral medications. Vaccination against influenza with an influenza vaccine is often recommended for high-risk groups, such as children and the elderly, or in people that have asthma, diabetes, or heart disease. However, it is possible to get vaccinated and still get influenza. The vaccine is reformulated each season for a few specific influenza strains but cannot possibly include all the strains actively infecting people in the world for that season. It takes about six months for the manufacturers to formulate and produce the millions of doses required to deal with the seasonal epidemics; occasionally, a new or overlooked strain becomes prominent during that time and infects people although they have been vaccinated (as by the H3N2 Fujian flu in the 2003-2004 influenza season). It is also possible to get infected just before vaccination and get sick with the very strain that the vaccine is supposed to prevent, as the vaccine takes about two weeks to become effective.

Further, the effectiveness of these influenza vaccines is variable. Due to the high mutation rate of the virus, a particular influenza vaccine usually confers protection for no more than a few years. A vaccine formulated for one year may be ineffective in the following year, since the influenza virus changes rapidly over time, and different strains become dominant.

Because of the absence of RNA proofreading enzymes, the RNA-dependent RNA polymerase of influenza vRNA makes a single nucleotide insertion error roughly every 10 thousand nucleotides, which is the approximate length of the influenza vRNA. Hence, nearly every newly-manufactured influenza virus is a mutant-antigenic drift. The separation of the genome into eight separate segments of vRNA allows mixing or reassortment of vRNAs if more than one viral line has infected a single cell. The resulting rapid change in viral genetics produces antigenic shifts and allows the virus to infect new host species and quickly overcome protective immunity.

Antiviral drugs can also be used to treat influenza, with NA inhibitors being particularly effective, but viruses can develop resistance to the approved NA antiviral drugs. Also, emergence of a multidrug-resistant pandemic influenza A viruses has been well documented. Drug-resistant pandemic influenza A becomes a substantial public health threat. In addition to the drug resistant influenza A viruses, the NA inhibitors are approved for the treatment early influenza infection (within 48 hours of influenza symptom onset).

Thus, there is still a need for drugs for treating influenza infections, such as for drugs with expanded treatment window, and/or reduced sensitivity to viral titer.

SUMMARY

The present disclosure generally relates to methods of treating influenza, to methods of inhibiting the replication of influenza viruses, to methods of reducing the amount of influenza viruses, and to compounds and compositions that can be employed for such methods.

Provided herein are methods of treating or preventing influenza infection or replication in a subject in need thereof comprising administering to the subject a therapeutically effective amount of (1) 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof, and (2) a second influenza therapeutic agent selected from the group consisting of baloxavir marboxil, baloxavir, a neuraminidase inhibitor, and favipiravir, or a pharmaceutically acceptable salt or solvate thereof.

Further, the disclosure provides a combination comprising (1) 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof, and (2) baloxavir or baloxavir marboxil , or a pharmaceutically acceptable salt or solvate thereof; and (3) a neuraminidase inhibitor, such as oseltamivir, oseltamivir acid, zanamivir, laninamivir, peramivir, or a pharmaceutically acceptable salt or solvate thereof.

Further provided are methods of administering to a biological sample or patient a safe and effective amount of a combination as disclosed herein.

Also provided herein are methods of reducing the amount of influenza viruses in a biological sample or in a patient by administering to said biological sample or patient a safe and effective amount of a combination as disclosed herein.

Further provided are methods of treating or preventing an Influenza A or Influenza B infection in a patient, comprising administering to said patient a safe and effective amount of a combination as disclosed herein.

Also provided are uses of a combination described herein for inhibiting or reducing the replication of influenza viruses in a biological sample or patient, for reducing the amount of influenza viruses in a biological sample or patient, or for treating influenza in a patient.

Further provided herein are uses of a combination described herein for the manufacture of a medicament for treating influenza in a patient, for reducing the amount of influenza viruses in a biological sample or in a patient, or for inhibiting the replication of influenza viruses in a biological sample or patient.

The combinations disclosed herein can be co-formulated or can be separately administered to the subject, patient, or host.

BRIEF DESCRIPTION OF THE DRAWINGS

FIG. 1 is a MacSynergy™ II graph showing the effect of combinations of Compound 1 and baloxavir in an assay of replication of influenza virus A/PR/8/34 (H1N1) in MDCK cells. Synergy/antagonism are shown compared to 95% confidence intervals. Throughout, Compound 1 refers to 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid.

FIG. 2 is a MacSynergy™ II graph showing the effect of combinations of Compound 1 and oseltamivir acid in an assay of replication of influenza virus A/PR/8/34 (H1N1) in MDCK cells. Synergy/antagonism are shown compared to 95% confidence intervals.

FIG. 3 a MacSynergy™ II graph showing the effect of combinations of Compound 1 and favipiravir in an assay of replication of influenza virus A/PR/8/34 (H1N1) in MDCK cells. Synergy/antagonism are shown compared to 95% confidence intervals.

DETAILED DESCRIPTION

Disclosed herein are combinations of anti-influenza compounds (antiviral agents), and uses of these combinations, in inhibiting influenza virus activity. In some aspects, the present disclosure is generally related to the use of the combinations described herein for inhibiting the replication of influenza viruses in a biological sample or in a patient, for reducing the amount of influenza viruses (reducing viral titer) in a biological sample or in a patient, and for treating or preventing influenza in a patient. The combinations disclosed herein can be co-formulated or can be separately administered to the subject, patient, or host.

The combinations comprise, among other things, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof as an effective ingredient, alternatively referred to herein as "Compound 1". This compound is believed to be a CAP-binding PB2 domain inhibitor.

In various embodiments, Compound 1 is used in combination with a second antiviral agent as a prophylactic or therapeutic against influenza, e.g., against influenza virus replication or infection. The influenza can be a pandemic or drug-resistant pandemic/seasonal influenza virus. In some cases, the influenza is influenza A or influenza B. The second antiviral agent can be a polymerase inhibitor, a endonuclease inhibitor, or a neuraminidase inhibitor, or a flu vaccine. Further discussion regarding timing of administration of Compound 1 and the second antiviral agent is provided below.

In some aspects, there is provided a combination comprising 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and a second antiviral agent, and in some cases, the second antiviral agent is selected from the group consisting of baloxavir, baloxavir marboxil, a neuraminidase inhibitor, and favipravir, or a pharmaceutically acceptable salt or solvate thereof.

When separately administered, the administration of Compound 1 and a second antiviral agent can be simultaneous (e.g., within about 5-10 mintues of each other), or separated by 1 or more hours (e.g., 1 hour, 2 hours, 3 hours, 4 hours, 5 hours, 6 hours, 7 hours, 8 hours, 9 hours, 10 hours, 11 hours, 12 hours, 24 hours, 26 hours, 48 hours, or 72 hours). In some cases, Compound 1 can be administered before the second antiviral agent. In some other cases, Compound 1 can be administered after the second antiviral agent. Further discussion regarding timing of administration of Compound 1 and the second antiviral agent is provided below.

In other aspects, there is provided a combination comprising a) a therapeutically effective amount of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and b) a therapeutically effective amount of a second antiviral agent, and in some cases, the second antiviral agent is selected from the group consisting of baloxavir, baloxavir marboxil, a neuraminidase inhibitor, and favipiravir, or a pharmaceutically acceptable salt or solvate thereof.

In other aspects, there is provided use of a therapeutically effective amount of a combination as disclosed herein for the treatment or prevention of influenza virus infection or replication in a human patient. For example, the influenza virus can be a pandemic or drug-resistant pandemic/seasonal influenza virus. In some cases, the influenza virus can be influenza A or influenza B. Other flu viruses are described below.

In other aspects, there is provided use of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof in combination with a second antiviral agent, and in some cases, the second antiviral agent is selected from the group consisting of baloxavir, baloxavir marboxil, a neuraminidase inhibitor, and favipravir, or a pharmaceutically acceptable salt or solvate thereof, in the manufacture of a medicament for treatment or prevention of influenza virus infection or replication.

In other aspects, there is provided use of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof in combination with a second antiviral agent, and in some cases, the second antiviral agent is selected from the group consisting of baloxavir, baloxavir marboxil, a neuraminidase inhibitor, and favipravir, or a pharmaceutically acceptable salt or solvate thereof to inhibit influenza virus infection or replication.

In other aspects, there is provided a method for treatment or prevention of influenza virus infection or replication, comprising administering to a human patient having or at risk of influenza virus infection a combination of: a) a therapeutically effective amount of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof, and b) a therapeutically effective amount of a second antiviral agent, which in some cases is selected from the group consisting of baloxavir, baloxavir marboxil, a neuraminidase inhibitor, and favipravir, or a pharmaceutically acceptable salt or solvate thereof.

In other aspects, there is provided a method for treating or preventing influenza virus infection or replication, comprising administering to a human patient having or at risk of influenza infection 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof in a dose of about 10-1,000 mg/kg and a therapeutically effective amount of a second antiviral agent, which in some cases is selected from the group consisting of baloxavir, baloxavir marboxil, a neuraminidase inhibitor, and favipravir, or a pharmaceutically acceptable salt or solvate thereof.

In other aspects, there is provided a pharmaceutical composition for treatment or prevention of influenza virus infection or replication in a patient, comprising 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof as an effective ingredient, wherein the composition is administered in combination with a second antiviral agent, and in some cases, the second antiviral agent is selected from the group consisting of baloxavir, baloxavir marboxil, a neuraminidase inhibitor, and favipravir, or a pharmaceutically acceptable salt or solvate thereof.

In other aspects, there is provided a method of inhibiting endonuclease activity of influenza polymerase in an influenza A or B virus, comprising contacting the virus with a combination of Compound 1 and a second antiviral agent as disclosed herein.

In other aspects, there is provided a method for treating or preventing an Influenza A or Influenza B infection in a host, comprising administering to the host a therapeutic amount of a combination of Compound 1 and a second antiviral agent as disclosed herein.

In other aspects, there is provided a method for reducing endonuclease activity of influenza polymerase in an influenza A or B virus in a host, comprising administering to the host a therapeutic amount of a combination of Compound 1 and a second antiviral agent as disclosed herein.

In other aspects, there is provided a method for reducing influenza virus replication in a host, comprising administering to the host a therapeutic amount of a combination of Compound 1 and a second antiviral agent as disclosed herein.

In some embodiments, there are provided methods of use of a combination of Compound 1 and a second antiviral agent as disclosed, which further comprise contacting the influenza virus with or administering to the host a therapeutically effective amount of a third antiviral agent. For example, in some embodiments, the methods can further comprise administering to the host an influenza vaccine before, after, or concurrently with the combination. In some cases, the disclosed methods comprise administering Compound 1 and an influenza vaccine without another antiviral agent (i.e., the vaccine is the second antiviral agent). In some cases, Compound 1 is administered at the same time as the influenza vaccine. In some cases, Compound 1 is co-formulated with the influenza vaccine.

In other aspects, there is provided a use of a combination of Compound 1 and a second antiviral agent as disclosed herein in a treatment for an Influenza A or Influenza B virus infection.

In other aspects, there is provided a use of a combination of Compound 1 and a second antiviral agent as disclosed herein in the manufacture of a medicament for the treatment of an Influenza A or Influenza B virus infection.

In other aspects, there is provided a combination comprising a) 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof, b) baloxavir, baloxavir marboxil, or a pharmaceutically acceptable salt or solvate thereof, and c) a neuraminidase inhibitor.

A neuraminidase inhibitor for use in the methods disclosed herein can be oseltamivir, oseltamivir acid, zanamavir (Relenzar .), laninamivir (inavirq, or perarn vir, or a pharmaceutically acceptable salt or solvate thereof. An endonuclease inhibitor can be used in the methods disclosed herein, and in some cases an endonuclease inhibitor is refered to as a "PA" inhibitor. In various embodiments, the endonuclease inhibitor can be baloxavir or baloxavir marboxil or a pharmaceutically acceptable salt or solvate thereof. A polymerase inhibitor can be used in the methods disclosed herein, and in some cases, a polymerase inhibitor is refered to as a "PB1" inhibitor. In various embodiments, the polymerase inhibitor can be favipravir, or a pharmaceutically acceptable salt or solvate thereof. A influenza vaccine can be used in the methods disclosed herein.

In various embodiments of aspects disclosed herein, the second antiviral agent is baloxavir, baloxavir marboxil, or a pharmaceutically acceptable salt or solvate thereof. In other embodiments of aspects disclosed herein, the second antiviral agent is a neuraminidase inhibitor (e.g., more specifically, oseltamivir, oseltamivir acid, or a pharmaceutically acceptable salt or solvate thereof). In other embodiments of aspects disclosed herein, the second antiviral agent is favipravir, or a pharmaceutically acceptable salt or solvate thereof.

Methods of Use

The combinations described herein can be used to reduce viral titer in a biological sample (e.g., an infected cell culture) or in humans (e.g., lung viral titer in a patient).

The terms "influenza virus mediated condition," "influenza infection," or "Influenza," as used herein, are used interchangeably to mean the disease caused by an infection with an influenza virus.

Influenza is an infectious disease that affects birds and mammals caused by influenza viruses. Influenza viruses are RNA viruses of the family Orthomyxoviridae, which comprises five genera: Influenza virus A, Influenza virus B, Influenza virus C, Isavirus and Thogotovirus. Influenza virus A genus has one species, influenza A virus which can be subdivided into different serotypes based on the antibody response to these viruses: H1N1, H2N2, H3N2, H5N1, H7N7, H1N2, H9N2, H7N2, H7N3 H7N9, and H10N7. Influenza virus B genus has one species, influenza B virus. Influenza B almost exclusively infects humans and is less common than influenza A. Influenza virus C genus has one species, influenza virus C virus, which infects humans and pigs and can cause severe illness and local epidemics. However, influenza virus C is less common than the other types and usually seems to cause mild disease in children.

In some embodiments, influenza or influenza viruses are associated with influenza virus A or B. In some embodiments, influenza or influenza viruses are associated with Influenza virus A. In some specific embodiments, influenza virus A is H1N1, H2N2, H3N2, H7N9, or H5N1. In some embodiments, the disclosed combinations are effective to inhibit growth or replication of a pandemic or drug-resistant pandemic/seasonal influenza virus.

In humans, common symptoms of influenza are chills, fever, pharyngitis, muscle pains, severe headache, coughing, weakness, and general discomfort. In more serious cases, influenza causes pneumonia, which can be fatal, particularly in young children and the elderly. Although it is often confused with the common cold, influenza is a much more severe disease and is caused by a different type of virus. Influenza can produce nausea and vomiting, especially in children, but these symptoms are more characteristic of the unrelated gastroenteritis, which is sometimes called "stomach flu" or "24-hour flu".

Symptoms of influenza can start quite suddenly one to two days after infection. Usually the first symptoms are chills or a chilly sensation, but fever is also common early in the infection, with body temperatures ranging from 38-39° C. (approximately 100-103° F.). Many people are so ill that they are confined to bed for several days, with aches and pains throughout their bodies, which are worse in their backs and legs. Symptoms of influenza may include: body aches, especially joints and throat, extreme coldness and fever, fatigue, Headache, irritated watering eyes, reddened eyes, skin (especially face), mouth, throat and nose, abdominal pain (in children with influenza B). Symptoms of influenza are non-specific, overlapping with many pathogens ("influenza-like illness"). Usually, laboratory data is needed to confirm the diagnosis.

The terms "disease," "disorder," and "condition" may be used interchangeably herein to refer to an influenza virus mediated medical or pathological condition.

As used herein, the terms "subject," "host," and "patient" are used interchangeably. The terms "subject", "host", and "patient" may refer to an animal (e.g., a bird such as a chicken, quail or turkey, or a mammal), specifically a mammal, such as a non-primate (e.g., a cow, pig, horse, sheep, rabbit, guinea pig, rat, cat, dog, or mouse) or a primate (e.g., a monkey, chimpanzee, or human), and more specifically a human. In some embodiments, the subject is a non-human animal such as a farm animal (e.g., a horse, cow, pig or sheep), or a pet (e.g., a dog, cat, guinea pig or rabbit). In a preferred embodiment, the subject is a human.

The term "biological sample," as used herein, includes, without limitation, cell cultures or extracts thereof; biopsied material obtained from a mammal or extracts thereof; blood, saliva, urine, feces, semen, tears, or other body fluids or extracts thereof.

As used herein the term "inhibition of the replication of influenza viruses" includes both the reduction in the amount of virus replication (e.g., areduction by at least 10%) up to and including the complete arrest of virus replication (i.e., 100% reduction in the amount of virus replication). In some embodiments, the replication of influenza viruses is inhibited by at least 50%, at least 65%, at least 75%, at least 85%, at least 90%, or at least 95%.

Influenza virus replication can be measured by any suitable method known in the art. For example, influenza viral titer in a biological sample (e.g., an infected cell culture) or in humans (e.g., lung viral titer in a patient) can be measured. More specifically, for cell-based assays, in each case cells are cultured in vitro, virus is added to the culture in the presence or absence of a test agent, and after a suitable length of time a virus-dependent endpoint is evaluated. For typical assays, the Madin-Darby canine kidney cells (MDCK) and the standard tissue culture adapted influenza strain, A/Puerto Rico/8/34 can be used. A first type of cell assay that can be used depends on death of the infected target cells, a process called cytopathic effect (CPE), where virus infection causes exhaustion of the cell resources and eventual lysis of the cell. In the first type of cell assay, a low fraction of cells in the wells of a microtiter plate are infected (typically 1/10 to 1/1000), the virus is allowed to go through several rounds of replication over 48-72 hours, then the amount of cell death is measured using a decrease in cellular ATP content compared to uninfected controls. A second type of cell assay that can be employed depends on the multiplication of virus-specific RNA molecules in the infected cells, with RNA levels being directly measured using the branched-chain DNA hybridization method (bDNA). In the second type of cell assay, a low number of cells are initially infected in wells of a microtiter plate, the virus is allowed to replicate in the infected cells and spread to additional rounds of cells, then the cells are lysed, and viral RNA content is measured. This assay is stopped early, usually after 18-36 hours, while all the target cells are still viable. Viral RNA is quantitated by hybridization to specific oligonucleotide probes fixed to wells of an assay plate, then amplification of the signal by hybridization with additional probes linked to a reporter enzyme.

As used herein a "viral titer" or "titer" is a measure of virus concentration. Titer testing can employ serial dilution to obtain approximate quantitative information from an analytical procedure that inherently only evaluates as positive or negative. The titer corresponds to the highest dilution factor that still yields a positive reading; for example, positive readings in the first 8 serial twofold dilutions translate into a titer of 1:256. A specific example is viral titer. To determine the titer, several dilutions will be prepared, such as $10^{-1}, 10^{-2}, 10^{-3}, \ldots, 10^{-8}$. The lowest concentration of virus that still infects cells is the viral titer.

As used herein, the terms "treat", "treatment," and "treating" refer to both therapeutic and prophylactic treatments. For example, therapeutic treatments include the reduction or amelioration of the progression, severity and/or duration of influenza virus-mediated conditions, or the amelioration of one or more symptoms (specifically, one or more discernible symptoms) of influenza virus-mediated conditions, resulting from the administration of one or more therapies (e.g., one or more therapeutic agents such as a compound or composition described herein). In specific embodiments, the therapeutic treatment includes the amelioration of at least one measurable physical parameter of an influenza virus-mediated condition. In other embodiments, the therapeutic treatment includes the inhibition of the progression of an influenza virus-mediated condition, either physically by, e.g., stabilization of a discernible symptom, physiologically by, e.g., stabilization of a physical parameter, or both. In other embodiments, the therapeutic treatment includes the reduction or stabilization of influenza viruses mediated infections. Antiviral drugs can be used in the community setting to treat people who already have influenza to reduce the severity of symptoms and reduce the number of days that they are sick.

The terms "prophylaxis," "prophylactic", "prophylactic use," and "prophylactic treatment," as used herein, refer to any medical or public health procedure whose purpose is to prevent, rather than treat or cure a disease. As used herein, the terms "prevent," "prevention," and "preventing" refer to the reduction in the risk of acquiring or developing a given condition, or the reduction or inhibition of the recurrence or said condition in a subject who is not ill, but who has been or may be near a person with the disease. The term "chemoprophylaxis" refers to the use of medications, e.g., small molecule drugs, rather than vaccines for the prevention of a disorder or disease.

Prophylactic use includes use in situations in which an outbreak has been detected to prevent contagion or spread of the infection in places where many people that are at high risk of serious influenza complications live in close contact with each other (e.g., in a hospital ward, daycare center, prison, nursing home, etc.). It also includes the use among populations who require protection from influenza but who do not get protection after vaccination (e.g., due to weak immune system), to whom the vaccine is unavailable, or who cannot receive the vaccine because of side effects. It also includes use during the two weeks following vaccination, or during any period after vaccination but before the vaccine is effective. Prophylactic use may also include treating a person who is not ill with the influenza or not considered at high risk for complications, to reduce the chances of getting infected with the influenza and passing it on to a high-risk person in close contact with him or her (e.g., healthcare workers, nursing home workers, etc.).

As used herein, and consistent with the usage of the United States Centers for Disease Control and Prevention (US CDC), an influenza "outbreak" is defined as a sudden increase of acute febrile respiratory illness (AFRI) occurring within a 48- to 72-hour period, in a group of people who are near each other (e.g., in the same area of an assisted living facility, in the same household, etc.) over the normal background rate or when any subject in the population being analyzed tests positive for influenza.

In some embodiments, the combinations are useful as a preventative or prophylactic measure to a patient, specifically a human, having a predisposition to complications resulting from infection by an influenza virus. The combinations can be useful in prophylactic methods in situations in which an index case or an outbreak has been confirmed, to prevent the spread of infection in the rest of the community or population group.

As used herein, an "effective amount" refers to an amount sufficient to elicit the desired biological response. In the present disclosure the desired biological response is to inhibit the replication of influenza virus, to reduce the amount of influenza virus, or to reduce or ameliorate the severity, duration, progression, or onset of an influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and on the characteristics of the subject, such as general health, age, sex, body weight and tolerance to drugs. The skilled artisan will be able to determine appropriate dosages depending on these and other factors.

Thus, when 3-(2-(5-chloro-1H-pyrrolo[2,3-b]pyridin-3-yl)-5-fluoro-7H-pyrrolo[2,3-d]pyrimidin-7-yl)bicyclo [2.2.2]octane-2-carboxylic acid is co-administered with other antiviral agents, e.g., when co-administered with an anti-influenza medication, an effective amount of the second agent will depend on the type of drug used. A safe amount is one with minimal or an acceptable number and severity of side effects, as can readily be determined by those skilled in the art. Suitable dosages are known for approved agents and can be adjusted by the skilled artisan according to the condition of the subject, the type of condition(s) being treated, and the amount of a compound described herein being used. In cases where no amount is expressly noted, a safe and effective amount should be assumed. For example, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof can be administered to a subject in a dosage range from between approximately 0.01 to 100 mg/kg body weight/day for therapeutic or prophylactic treatment.

As used herein, a "safe and effective amount" of a compound or composition described herein is an effective amount of the compound or composition which does not cause excessive or deleterious side effects in a patient.

Generally, dosage regimens can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe a safe and effective amount of the compounds described herein required to treat, to prevent, inhibit (fully or partially) or arrest the progress of the disease.

Dosages of the compounds described herein can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosing, such as twice a day (e.g., every 12 hours), three times a day (e.g., every 8 hours), or four times a day (e.g., every 6 hours).

For therapeutic treatment, the compounds described herein can be administered to a patient within, for example, 48 hours (or within 40 hours, or less than 2 days, or less than 1.5 days, or within 24 hours) of onset of symptoms (e.g., nasal congestion, sore throat, cough, aches, fatigue, headaches, and chills/sweats). The therapeutic treatment can last for any suitable duration, for example, for 5 days, 7 days, 10 days, 14 days, etc. For prophylactic treatment during a community outbreak, the compounds described herein can be administered to a patient within, for example, 2 days of onset of symptoms in the index case, and can be continued for any suitable duration, for example, for 7 days, 10 days, 14 days, 20 days, 28 days, 35 days, 42 days, etc.

Combination Therapy

A combination described herein can be administered alone or in further combination with an additional suitable therapeutic agent, for example, a third antiviral agent or a vaccine. When combination therapy is employed, a safe and effective amount can be achieved using a first amount of Compound 1, i.e., 3-(2-(5-chloro-1H-pyrrolo[2,3-b]pyridin-3-yl)-5-fluoro-7H-pyrrolo[2,3-d]pyrimidin-7-yl)bicyclo [2.2.2]octane-2-carboxylic acid, or a pharmaceutically acceptable salt or solvate thereof, the second antiviral agent, and an amount of one or more of third antiviral agents. In some cases, the third antiviral agent is a pyrazinecarboxamide antiviral compound, an influenza neuraminidase inhibitor, or an influenza PB1 polymerase domain inhibitor. Further therapeutic combinations may be achieved with an additional suitable therapeutic agent (e.g., an antiviral agent or vaccine).

Among the second antiviral agents suitable for use in these combinations is baloxavir (CAS No. 1985605-59-1), which is under development as the marboxil prodrug (CAS No. 1985606-14-1; trade name Xofluza®), by Shionogi Co., a Japanese pharmaceutical company, for treatment of influenza A and influenza B.

Also among the second antiviral agents suitable for use in these combinations is Oseltamivir phosphate (CAS No. 204255-11-8; trade name (Tamiflu®), which is is a neuraminidase inhibitor being developed by Roche pharmaceutical company, as a medication for treatment or prevention of influenza infection.

Also among the second antiviral agents suitable for use in these combinations is favipiravir (CAS No. 259793-96-9; T-705; trade name Avigan®), which is a pyrazinecarboxamide derivative being developed by Toyama Chemical Co., Ltd., a Japanese pharmaceutical company, for treatment of RNA viruses, including influenza A and influenza B. Use of the 200 mg tablet to treat influenza is approved in Japan. For adults, favipiravir can be administered orally in amounts of from 10 mg to 10,000 mg per day. In some embodiments favipiravir can be administered orally in amounts of from 100 mg to 4,000 mg per day. In some embodiments favipiravir can be administered orally in amounts of 1,600 mg twice a day on Day 1, and 600 mg of favipiravir twice a day from Day 2 to Day 5, with the total administration period being five days.

Kitano et al. report that combinations of baloxavir with neuraminidase inhibitors synergistically inhibited the replication of influenza A/H1N1 virus in NOCK cells (*Open Forum Infectious Diseases*, 4, Issue suppl_1, 1 Oct. 2017, Pages S371). Accordingly, in some embodiments there is provided a combination comprising 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid and baloxavir or baloxavir marboxil and a neuraminidase inhibitor. Neuraminidase inhibitors suitable for use in such combinations, include, for example, oseltamivir, oseltamivir acid, zanamivir, laninamivir, and peramivir, or more specifically, oseltamivir phosphate, oseltamivir acid, zanamivir hydrate, laninamivir, and peramivir trihydrate.

In some embodiments of this disclosure, Compound 1, or a pharmaceutically acceptable salt thereof, and the second antiviral agent, are each administered in a safe and effective amount (i.e., each in an amount which would be therapeutically effective if administered alone). In some embodiments, Compound 1 and the second antiviral agent are each administered in an amount which alone does not provide a therapeutic effect (a sub-therapeutic dose). In some embodiments, Compound 1 can be administered in a safe and effective amount, while the second antiviral agent is administered in a sub-therapeutic dose. In some embodiments, Compound 1 can be administered in a sub-therapeutic dose, while the second antiviral agent is administered in a safe and effective amount.

As used herein, the terms "combination therapy", "in combination," and "co-administration," or "coadministration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Coadministration can encompass administration of the first and second amounts of the compounds of the combination in an essentially simultaneous manner, such as in a single pharmaceutical composition, for example, capsule or tablet having a fixed ratio of first and second amounts, or in multiple, separate capsules or tablets for each. In addition, such coadministration can also encompass use of each compound of the combination in a sequential manner in either order.

In some embodiments, the present disclosure is directed to methods of combination therapy for inhibiting influenza virus replication in biological samples or patients, or for treating or preventing influenza virus infections in patients using the compounds or pharmaceutical compositions of the disclosure. Accordingly, pharmaceutical compositions described herein also include those comprising 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid in combination with a second antiviral agent exhibiting anti-influenza virus activity.

Methods of use also include combination of Compound 1 and a second antiviral agent, in further combination with another anti-viral agent and/or vaccination with a flu vaccine.

When co-administration involves the separate administration of a first amount of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid and a second amount of a second antiviral agent, the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid and the second agent antiviral are administered sufficiently close in time to have the desired therapeutic effect. For example, the period between each administration can range from minutes to hours and can be selected by taking into account the properties of each compound such as potency, solubility, bioavailability, plasma half-life, and kinetic profile, to result in the desired therapeutic effect. For example, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid and a second antiviral agent can be administered in any order within about 24 hours of each other, within about 16 hours of each other, within about 8 hours of each other, within about 4 hours of each other, within about 1 hour of each other or within about 30 minutes of each other.

More specifically, the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid can be administered prior to (e.g., 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the second antiviral agentto a subject.

The method of co-administration of an amount of 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid and an amount of an a second antiviral agent as set forth herein can result in an enhanced or synergistic therapeutic effect, in which the observed combined effect is greater than the additive effect that would have been expected to result from separate administration of an amount of Compound 1 and an amount of a second antiviral agent.

As used herein, the term "synergistic" refers to a combination the disclosure which is more effective than the additive effects of the component compounds. A synergistic effect of a combination of therapies (e.g., a combination of prophylactic or therapeutic agents) can permit the use of lower dosages of one or more of the therapies and/or less frequent administration of said therapies to a subject. The ability to utilize lower dosages of a therapy (e.g., a prophylactic or therapeutic agent) and/or to administer said therapy less frequently can reduce the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

Furthermore, when the combination therapy the present disclosure is used, the component therapeutic agents can be administered so that the period between each administration can be longer (e.g., days, weeks, or months).

The presence of a synergistic effect can be determined using suitable methods for assessing drug interaction. Suitable methods include, for example, the Sigmoid-Emax equation (Holford, N. H. G. and Scheiner, L. B., *Clin. Pharmacokinet.* 6: 429-453 (1981)), the equation of Loewe additivity (Loewe, S, and Muischnek, H., *Arch. Exp. Pathol. Pharmacol.* 114: 313-326 (1926)) and the median-effect equation (Chou, T. C. and Talalay, P., Adv. *Enzyme Regul.* 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively. MacSynergy ™ II is a well-established graphic software useful for calculating combination indices (Prichard and Shipman, 1990).

Anti-influenza Vaccines

The compounds described herein can be prophylactically administered in conjunction with anti-influenza vaccines. These vaccines can be administered, for example, via subcutaneous or intranasal administration. Vaccination via subcutaneous injection typically induces an IgG antibody having a neutralizing activity in the serum, and is highly effective for preventing progression of the condition into a more severe one such as pneumonia and the like. However, in the upper airway mucosa, which is the infection site, IgA is the main prophylactic component. Since IgA is not induced by subcutaneous administration, it can also be advantageous to administer vaccines via an intranasal route.

Definitions and General Terminology

The compounds described herein are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts and Solvates

The compounds described herein can exist in free form, or, where appropriate, as salts. Those salts that are pharmaceutically acceptable are of particular interest since they are useful in administering the compounds that are components of the described combinations for medical purposes. Salts that are not pharmaceutically acceptable are useful in manufacturing processes, for isolation and purification purposes, and in some instances, for use in separating stereoisomeric forms of the compounds described herein or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences,* 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxylic acid group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C_{1-4}alkyl)_4$ salts. This disclosure also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminum. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminum hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N,N'-dibenzyl-ethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

This components of the combinations can include mixtures/combinations of different pharmaceutically acceptable salts and mixtures/combinations of compounds in free form and pharmaceutically acceptable salts.

The components of the combinations can be present in the form of a solvate. The term "solvate" refers to a molecular complex of a compound (including a salt thereof) with one or more solvent molecules. Such solvent molecules are those commonly used in the pharmaceutical art, which are known to be innocuous to a recipient, e.g., water, ethanol, dimethylsulfoxide, acetone and other common organic solvents. The term "hydrate" refers to a molecular complex comprising a compound and water.

Pharmaceutical Compositions

The compounds described herein can be formulated into pharmaceutical compositions that further comprise a pharmaceutically acceptable carrier, diluent, adjuvant or vehicle. In some embodiments, the present disclosure relates to a pharmaceutical composition comprising a compound described herein, and a pharmaceutically acceptable carrier, diluent, adjuvant or vehicle. In some embodiments, the present disclosure includes a pharmaceutical composition comprising a safe and effective amount of a compound described herein or a pharmaceutically acceptable salt thereof and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

An "effective amount" includes a "therapeutically effective amount" and a "prophylactically effective amount." The term "therapeutically effective amount" refers to an amount effective in treating and/or ameliorating an influenza virus infection in a patient. The term "prophylactically effective amount" refers to an amount effective in preventing and/or substantially lessening the chances or the size of influenza virus infection outbreak.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington's Pharmaceutical Sciences,* 16th ed., E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds described herein, such as by producing any undesirable biological effect or otherwise interacting in a deleterious manner with any other component(s) of the pharmaceutically acceptable composition, its use is contemplated to be within the scope of this disclosure.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

Some examples of materials which can serve as pharmaceutically acceptable carriers include, but are not limited to, ion exchangers, alumina, aluminum stearate, lecithin, serum proteins (such as human serum albumin), buffer substances (such as twin 80, phosphates, glycine, sorbic acid, or potassium sorbate), partial glyceride mixtures of saturated vegetable fatty acids, water, salts or electrolytes (such as protamine sulfate, disodium hydrogen phosphate, potassium hydrogen phosphate, sodium chloride, or zinc salts), colloidal silica, magnesium trisilicate, polyvinyl pyrrolidone, polyacrylates, waxes, polyethylene-polyoxypropylene-block polymers, methylcellulose, hydroxypropyl methylcellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and anti-oxidants can also be present in the composition, according to the judgment of the formulator.

Formulations for Pulmonary Delivery

In some embodiments, the pharmaceutical compositions described herein are adapted to be administered to the lower respiratory tract (e.g., the lungs) directly through the airways by inhalation. Compositions for administration by inhalation may take the form of inhalable powder compositions or liquid or powder sprays, and can be administered in standard form using powder inhaler devices or aerosol dispensing devices. Such devices are well known. For administration by inhalation, the powdered formulations typically comprise the active compound together with an inert solid powdered diluent such as lactose or starch. Inhalable dry powder compositions may be presented in capsules and cartridges of gelatin or a like material, or blisters of laminated aluminum foil for use in an inhaler or insufflators. Each capsule or cartridge may generally contain e.g., from about 10 mg to about 100 g of each active compound. Alternatively, the composition described herein may be presented without excipients.

The inhalable compositions may be packaged for unit dose or multi-dose delivery. For example, the compositions can be packaged for multi-dose delivery in a manner analogous to that described in GB 2242134, U.S. Pat. Nos. 6,632,666, 5,860,419, 5,873,360, and 5,590,645 (all illustrating the "Diskus" device), or GB2i78965, GB2129691, GB2169265, U.S. Pat. Nos. 4,778,054, 4,811,731 and 5,035, 237 (which illustrate the "Diskhaler" device), or EP 69715 ("Turbuhaler" device), or GB 2064336 and U.S. Pat. No. 4,353,656 ("Rotahaler" device).

Spray compositions for topical delivery to the lung by inhalation may be formulated as aqueous solutions or suspensions or as aerosols delivered from pressurized packs, such as a metered dose inhaler (MDI), with the use of a suitable liquefied propellant, including hydrofluoroalkanes such as dichlorodifluoromethane, trichlorofluoromethane, dichlorotetrafluoroethane, and especially 1,1,1,2-tetrafluoroethane, 1,1,1,2,3,3,3-heptafluoro-n-propane and mixtures thereof. Aerosol compositions suitable for inhalation can be presented either as suspensions or as solutions.

Medicaments for administration by inhalation typically have a controlled particle size. The optimum particle size for inhalation into the bronchial system is usually about 1 to about 10 μm, and in some embodiments, from about 2 to about 5 pm. Particles having a size above about 20 pm are generally too large when inhaled to reach the small airways. To achieve these particle sizes the particles of the active ingredient may be subjected to a size reducing process such as micronization. The desired size fraction may be separated out by air classification or sieving. Preferably, the particles will be crystalline.

Intranasal sprays may be formulated with aqueous or non-aqueous vehicles with the addition of agents such as thickening agents, buffer salts or acid or alkali to adjust the pH, isotonic adjusting agents or anti-oxidants.

Solutions for inhalation by nebulization may be formulated with an aqueous vehicle with the addition of agents such as acid or alkali, buffer salts, isotonic adjusting agents or antimicrobial agents. They may be sterilized by filtration or heating in an autoclave, or presented as a non-sterile product. Nebulizers supply the aerosol as a mist created from an aqueous formulation.

In some embodiments, the pharmaceutical compositions described herein can be formulated with supplementary active ingredients.

In some embodiments, the pharmaceutical composition described herein is administered from a dry powder inhaler.

In other embodiments, the pharmaceutical composition described herein is administered by an aerosol dispensing device, optionally in conjunction with an inhalation chamber such as the "Volumatic"® inhalation chamber.

The carrier can be a solvent or dispersion medium containing, for example, water, ethanol, polyol (for example, glycerol, propylene glycol and liquid polyethylene glycol, and the like), suitable mixtures thereof, and/or vegetable oils. The proper fluidity can be maintained, for example, by the use of a coating such as, for example, lecithin, by the maintenance of the required particle size in the case of dispersion and by the use of surfactants. Preventing the action of microorganisms in the compositions described herein is achieved by adding antibacterial and/or antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

In some embodiments, a pharmaceutical composition described herein can be within a matrix which controls the release of the composition. In some embodiments, the matrix can comprise lipid, polyvinyl alcohol, polyvinyl acetate, polycaprolactone, poly(glycolic)acid, poly(lactic) acid, polycaprolactone, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and combinations thereof and other polymers such as those disclosed, for example, in U.S. Pat. Nos. 6,667,371; 6,613,355; 6,596,296; 6,413,536; 5,968,543; 4,079,038; 4,093,709; 4,131,648; 4,138,344; 4,180,646; 4,304,767; 4,946,931, each of which is expressly incorporated by reference herein in its entirety. In these embodiments, the matrix sustainedly releases the drug.

Pharmaceutically acceptable carriers and/or diluents may also include any solvents, dispersion media, coatings, antibacterials and/or antifungals, isotonic and absorption delaying agents and the like. The use of such media and agents for pharmaceutically active substances is well known in the art. Except insofar as any conventional medium or agent is incompatible with the active ingredient, use thereof in the pharmaceutical compositions is contemplated.

The pharmaceutical compositions described herein can be formulated for administration in accordance with conventional techniques. See, e.g., Remington, *The Science and Practice of Pharmacy* (20th Ed. 2000). For example, the intranasal pharmaceutical compositions of the present disclosure can be formulated as an aerosol (this term includes both liquid and dry powder aerosols). Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles (e.g., lyophilized, freeze dried, etc.) can likewise be produced with any solid particulate medicament aerosol generator, by techniques known in the pharmaceutical art. As another example, the pharmaceutical compositions of the present disclosure can be formulated as an on-demand dissolvable form, which provides a lyophilized portion of the pharmaceutical composition and a dissolving solution portion of the pharmaceutical composition.

In some embodiments of the present disclosure, the pharmaceutical composition is in the form of an aqueous suspension, which can be prepared from solutions or suspensions. With respect to solutions or suspensions, dosage forms can be comprised of micelles of lipophilic substances, liposomes (phospholipid vesicles/membranes) and/or a fatty acid (e.g., palmitic acid). In particular embodiments, the pharmaceutical composition is a solution or suspension that is capable of dissolving in the fluid secreted by mucous membranes of the epithelium of the tissue to which it is administered, applied and/or delivered, which can advantageously enhance absorption.

The pharmaceutical composition can be an aqueous solution, a nonaqueous solution or a combination of an aqueous and nonaqueous solution.

Suitable aqueous solutions include, but are not limited to, aqueous gels, aqueous suspensions, aqueous microsphere suspensions, aqueous microsphere dispersions, aqueous liposomal dispersions, aqueous micelles of liposomes, aqueous microemulsions, and any combination of the foregoing, or any other aqueous solution that can dissolve in the fluid secreted by the mucosal membranes of the nasal cavity. Exemplary nonaqueous solutions include, but are not limited to, nonaqueous gels, nonaqueous suspensions, nonaqueous microsphere suspensions, nonaqueous microsphere dispersions, nonaqueous liposomal dispersions, nonaqueous emulsions, nonaqueous microemulsions, and any combination of the foregoing, or any other nonaqueous solution that can dissolve or mix in the fluid secreted by mucosal membranes.

Examples of powder formulations include, without limitation, simple powder mixtures, micronized powders, freeze dried powder, lyophilized powder, powder microspheres, coated powder microspheres, liposomal dispersions, and any combination of the foregoing. Powder microspheres can be formed from various polysaccharides and celluloses, which include without limitation starch, methylcellulose, xanthan gum, carboxymethylcellulose, hydroxypropyl cellulose, carbomer, alginate polyvinyl alcohol, acacia, chitosans, and any combination thereof.

In particular embodiments, the inhalable composition is one that is at least partially, or even substantially (e.g., at least 80%, 90%, 95% or more) soluble in the fluids that are secreted by mucosa to facilitate absorption. The composition can be formulated with a carrier and/or other substances that foster dissolution of the agent within secretions, including without limitation fatty acids (e.g., palmitic acid), gangliosides (e.g., GM-1), phospholipids (e.g., phosphatidylserine), and emulsifiers (e.g., polysorbate 80).

Those skilled in the art will appreciate that for intranasal administration or delivery, because the volume of the pharmaceutical composition administered is generally small, nasal secretions may alter the pH of the administered dose since the range of pH in the nasal cavity can be as wide as 5 to 8. Such alterations can affect the concentration of un-ionized drug available for absorption. Accordingly, in representative embodiments, the pharmaceutical composition further comprises a buffer to maintain or regulate pH in situ. Typical buffers include, but are not limited to, ascorbate, acetate, citrate, prolamine, carbonate, and phosphate buffers.

In some embodiments, the pH of the pharmaceutical composition is selected so that the internal environment of the mucosal tissue after administration is neutral or acidic, which (1) can provide the active compound in an un-ionized form for absorption, (2) inhibits growth of pathogenic bacteria, which is more likely to occur in an alkaline environment, and (3) reduces the likelihood of irritation of the mucosa.

For liquid and powder sprays or aerosols, the pharmaceutical composition can be formulated to have any suitable and desired particle or droplet size. In illustrative embodiments, the majority and/or the mean size of the particles or droplets range from equal to or greater than about 1, 2.5, 5, 10, 15 or 20 microns and/or equal to or less than about 25, 30, 40, 45, 50, 60, 75, 100, 125, 150, 175, 200, 225, 250, 275, 300, 325, 350, 375, 400, or 425 microns (including all combinations of the foregoing). Representative examples of suitable ranges for the majority and/or mean particle or droplet size include, without limitation, from about 5 to 100 microns, from about 10 to 60 microns, from about 175 to 325 microns, and from about 220 to 300 microns which facilitate the deposition of a safe and effective amount of the active compound, for example, in the nasal cavity (e.g., in the upper third of the nasal cavity, the superior meatus, the olfactory region and/or the sinus region to target the olfactory neural pathway). In general, particles or droplets smaller than about 5 microns will be deposited in the trachea or even the lung, whereas particles or droplets that are about 50 microns or larger generally do not reach the nasal cavity and are deposited in the anterior nose.

International patent publication WO 2005/023335 describes particles and droplets having a diameter size suitable for the practice of representative embodiments of the present disclosure. In particular embodiments, the particles or droplets have a mean diameter of about 5 to 30 microns, about 10 to 20 microns, about 10 to 17 microns, about 10 to 15 microns, about 12 to 17 microns, about 10 to 15 microns or about 10 to 12 microns. The particles can "substantially" have a mean diameter or size as described herein, i.e., at least about 50%, 60%, 70%, 80%, 90% or 95 or more of the particles are of the indicated diameter or size range.

The pharmaceutical composition described herein can be delivered as a nebulized or atomized liquid having a droplet size as described above.

According to particular embodiments that comprise methods of intranasal delivery, it can be desirable to prolong the residence time of the pharmaceutical composition in the nasal cavity (e.g., in the upper third of the nasal cavity, the superior meatus, the olfactory region and/or in the sinus region), for example, to enhance absorption. Thus, the pharmaceutical composition can optionally be formulated with a bioadhesive polymer, a gum (e.g., xanthan gum), chitosan (e.g., highly purified cationic polysaccharide), pectin (or any carbohydrate that thickens like a gel or emulsifies when applied to nasal mucosa), a microsphere (e.g., starch, albumin, dextran, cyclodextrin), gelatin, a liposome, carbamer, polyvinyl alcohol, alginate, acacia, a chitosan, and/or a cellulose (e.g., methyl or propyl; hydroxyl or carboxy; or carboxymethyl or hydroxypropyl cellulose), which are agents that enhance residence time in the nasal cavity. As a further approach, increasing the viscosity of the formulation can also provide a means of prolonging contact of the agent with the nasal epithelium. The pharmaceutical composition can be formulated as a nasal emulsion, ointment or gel, which offers advantages for local application because of their viscosity.

Moist and highly vascularized membranes can facilitate rapidabsorption. Consequently, the pharmaceutical composition can optionally comprise a humectant, particularly in the case of a gel-based composition to assure adequate intranasal moisture content. Examples of suitable humectants include but are not limited to glycerin or glycerol, mineral oil, vegetable oil, membrane conditioners, soothing agents, and/or sugar alcohols (e.g., xylitol, sorbitol; and/or mannitol). The concentration of the humectant in the pharmaceutical composition will vary depending upon the agent selected and the formulation.

The pharmaceutical composition can also optionally include an absorption enhancer, such as an agent that inhibits enzyme activity, reduces mucous viscosity or elasticity, decreases mucociliary clearance effects, opens tight junctions, and/or solubilizes the active compound. Chemical enhancers are known in the art and include chelating agents (e.g., EDTA), fatty acids, bile acid salts, surfactants, and/or preservatives. Enhancers for penetration can be particularly useful when formulating compounds that exhibit poor membrane permeability, lack of lipophilicity, and/or are degraded by aminopeptidases. The concentration of the absorption enhancer in the pharmaceutical composition will vary depending upon the agent selected and the formulation.

To extend shelf life, preservatives can optionally be added to the pharmaceutical composition. Suitable preservatives include but are not limited to benzyl alcohol, parabens, thimerosal, chlorobutanol, and benzalkonium chloride, and combinations of the foregoing. The concentration of the preservative will vary depending upon the preservative used, the compound being formulated, the formulation, and the like. In representative embodiments, the preservative is present in an amount of about 2% by weight or less.

The pharmaceutical compositions described herein can optionally contain an odorant, e.g., as described in EP 0 504 263 Bl, to provide a sensation of odor, to aid in inhalation of the composition to promote delivery to the olfactory region and/or to trigger transport by the olfactory neurons.

As another option, the composition can comprise a flavoring agent, e.g., to enhance the taste and/or acceptability of the composition to the subject.

Porous Particles for Pulmonary Administration

In some embodiments, the particles are porous, so that they have an appropriate density to avoid deposition in the back of the throat when administered via an inhaler. The combination of relatively large particle size and relatively low density avoids phagocytosis in the lungs, provides appropriately targeted delivery, avoids systemic delivery of the components, and provides a high concentration of the components in the lung.

Representative methods for preparing such particles, and for delivering such particles, are described, for example, in U.S. Pat. Nos. 7,384,649, 7,182,961, 7,146,978, 7,048,908, 6,956,021, 6,766,799, and 6,732,732.

Additional patents disclosing such particles include U.S. Pat. Nos. 7,279,182, 7,252,840, 7,032,593, 7,008,644, 6,848,197, and 6,749,835.

U.S. Pat. No. 7,678,364, discloses methods for delivering particles to the pulmonary system comprising: administering to the respiratory tract of a patient in need of treatment, prophylaxis or diagnosis a safe and effective amount of a dry powder comprising: a) a multivalent metal cation which is complexed with a therapeutic, prophylactic or diagnostic agent; b) a pharmaceutically acceptable carrier; and c) a multivalent metal cation-containing component in which the dry powder is spray-dried and has a total amount of multivalent metal cation which is about 10% w/w or more of the total weight of the agent, a tap density of about 0.4 g/cm³ or less, a median geometric diameter of from about 5 micrometers to about 30 micrometers and an aerodynamic diameter of from about 1 to about 5 microns.

The amount of the compounds described herein, or salts thereof, present in the particles can range from about 0.1 wt. % to about 95 wt. %, though in some cases, can even be as high as 100%. For example, from about 1 to about 50 wt. %, such as from about 5 to about 30 wt. %. Particles in which the drug is distributed throughout a particle can be preferred.

In some embodiments, the particles include a surfactant other than the phospholipids described above. As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to particles, they tend to present moieties to the external environment that do not attract similarly-coated particles, thus reducing particle agglomeration. Surfactants may also promote absorption of a therapeutic or diagnostic agent and increase bioavailability of the agent.

Suitable surfactants which can be employed in fabricating the particles described herein include but are not limited to hexadecanol; fatty alcohols such as polyethylene glycol (PEG); polyoxyethylene-9-lauryl ether; a surface-active fatty acid, such as palmitic acid or oleic acid; glycocholate; surfactin; a poloxamer; a sorbitan fatty acid ester such as sorbitan trioleate (Span 85); Tween® 80, and tyloxapol.

The surfactant can be present in the particles in an amount ranging from about 0 to about 5 wt. %. Preferably, it can be present in the particles in an amount ranging from about 0.1 to about 1 wt. %, e.g., 1.0 wt. %.

Particles that have a tap density less than about 0.4 g/cm³, median diameters of at least about 5 μm, and an aerodynamic diameter of from about 1 μm to about 5 μm, or from about 1 μm to about 3 μm, are more capable of escaping inertial and gravitational deposition in the oropharyngeal region, and are targeted to the airways or the deep lung. The use of larger, more porous particles is advantageous since they can be aerosolized more efficiently than smaller, denser particles such as those currently used for inhalation therapies.

Liposomal Delivery

The compositions described herein are advantageously delivered to the lungs, to provide the compounds at the site of an actual or potential influenza infection. This can be accomplished by pulmonary delivery via metered-dose inhalers or other pulmonary delivery devices, and also by lodging particles in the capillary beds surrounding the alveoli in the lungs.

Nanocarriers, such as liposomes, including small unilamellar vesicles, show several advantages over other conventional approaches for delivering drugs to the lungs, including prolonged drug release and cell-specific targeted drug delivery. Nano-sized drug carriers can also be advantageous for delivering poorly water-soluble drugs, and certain of the compounds described herein are poorly water-soluble. Additional advantages include their ability to provide controlled release, protection from metabolism and degradation, decreased drug toxicity and targeting capabilities.

The liposomes (preferably unilamellar vesicles) have a size less than 200 nm as measured by dynamic light scattering, and preferably characterized by being comprised of chemically pure synthetic phospholipids, most preferably having side chains of a length of at least 16 carbons, and containing one or more of the compounds described herein, or a pharmaceutically acceptable salt thereof, sufficient to preferentially deliver (i.e., target) a quantity of the compounds thereof to the capillary beds surrounding the alveoli. Vesicle diameter can be measured, for example, by dynamic light scattering using a helium-neon 100 mW NEC gas laser and a Malvern K7027 correlator, ideally with at least two or three measurements made for each for each size determination.

The expression "chemically pure phospholipids" is meant to define phospholipids which are essentially free of deleterious detergent moieties and impurities which cause aggregation of small unilamellar vesicles (SUVs) formed therefrom, and which are more than 97% pure. Preferably, the liposomes have a diameter predominantly of from about 50 to about 160 nm, are essentially neutral in charge, and incorporate phospholipids having a side chain length of from 16 to 18 carbon atoms. More preferably, the liposomes are prepared from distearoyl phosphatidylcholine (DSPC) and include cholesterol (most preferably in an amount of from 10 to 50% of total lipid) as a vesicle stabilizer.

It can also be advantageous that the liposomes have a melting point above body temperature (i.e., above 37° C.). For this reason, it can be advantageous to use pure phospholipids, preferably ones that are saturated, and have a carbon chain length of at least 16 carbons, preferably between 16 and 18 carbons. Distearoylphosphatidylcholine (DSPC) is a preferred phospholipid. Cholesterol helps to stabilize the liposomes and is preferably added in an amount sufficient to provide liposome stability. Most preferably, the liposomes further comprise a pegylated phospholipid, such as DSPEPEG. The method involves introducing into a patient's bloodstream an amount of liposomes, of a size of less than 200 nm (preferably unilamellar vesicles) and preferably characterized by being comprised of chemically pure synthetic phospholipids, most preferably having side chains of a length of at least 16 carbons, and containing the compounds described herein, or a pharmaceutically acceptable salt or prodrug thereof, sufficient to preferentially deliver (i.e., target) a quantity of the compounds to the capillary beds in the lungs, surrounding the alveoli.

The compounds described herein can be combined with other anti-influenza agents, as also described herein. Such additional agents can also be present in the liposomes, can be present in different liposomes, or can be co-administered via a different route.

The liposomes include one or more of the compounds described herein, or a pharmaceutically acceptable salt thereof, and can optionally include other anti-influenza agents. The liposomes can be prepared by dissolving the phospholipid and cholesterol in an appropriate organic solvent, such as chloroform, and evaporating the solvent to form a lipid film. If an ionophore is employed to load the compounds described herein into the liposomes, the ionophore may be added to the lipid solution before evaporation. The dried lipid film is then rehydrated in an appropriate aqueous phase, such as phosphate-buffered saline or other physiologically appropriate solution. Water-soluble drugs or therapeutic agents may be contained in the hydrating solution, although if remote loading is desired a loading agent such as a chelating agent described above may be added to the hydrating solution to be encapsulated within the inner aqueous space of the liposome.

Upon the addition of the hydrating solution, liposomes of varying size spontaneously form and encapsulate a portion of the aqueous phase. Thereafter, the liposomes and suspending aqueous solution are subjected to a shear force such as extrusion, sonication, or processing through a homogenizer according to the method described in U.S. Pat. No. 4,753,788; to produce vesicles within the specified size.

The liposomes can then be processed to remove undesirable compounds from the suspending solution, for example, un-encapsulated drug, which may be accomplished through processes such as gel chromatography or ultrafiltration.

The use of liposomes in dry powder aerosols for targeted lung delivery is described, for example, in Willis et al., *Lung*, June 2012, 190(3):251-262.

Administration Methods

The compounds and pharmaceutically acceptable compositions described above can be administered to humans and other animals orally, rectally, parenterally, intracisternally, intravaginally, intraperitoneally, topically (as by powders, ointments, or drops), bucally, as an oral or nasal spray, to the pulmonary system, such as by using an inhaler, such as a metered dose inhaler (MDI), or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

To prolong the effect of a compound described herein, it is often desirable to slow the absorption of the compound from subcutaneous or intramuscular injection. This may be accomplished by using a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsular matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this disclosure. Additionally, the present disclosure contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds described herein include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzalkonium chloride. Alternatively, for ophthalmic uses, the pharmaceutical compositions may be formulated in an ointment such as petrolatum.

The compounds for use in the methods described herein can be formulated in unit dosage form. The term "unit dosage form" refers to physically discrete units suitable for unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

The disclosure will be more fully understood by reference to the examples described herein which detail exemplary embodiments. These examples should not, however, be construed as limiting the scope of the disclosure. All citations throughout the disclosure are hereby expressly incorporated by reference.

EXAMPLES

Example 1—Cytopathic Effect Assay

A study was conducted to assess in vitro combination effects of a test compound 3-(2-(5-chloro-1H-pyrrolo[2,3- b]pyridin-3-yl)-5-fluoro-7H-pyrrolo[2,3-d]pyrimidin-7-yl)bicyclo[2.2.2]octane-2-carboxylic acid with other influenza antivirals in influenza virus cell-based assays for cytopathic effect (CPE).

Influenza virus A/PR/8/34 (H1N1) (ATCC VR-1469) was obtained from the ATCC. MDCK cells (ATCC CCL-34) were obtained from the ATCC and maintained in Minimal Essential Medium Eagle (Sigma M2279) supplemented with 10% fetal bovine serum (Corning R35-076-CV), 1% L-glutamine (Gibco 25030081), 1% non-essential amino acids (NEAA, Gibco 11140050), and 1% penicillin-streptomycin (PS, Hyclone SV30010).

The testing medium for MDCK cells was OptiPRO SFM medium (Gibco 12309019) supplemented with 1% L-glutamine, 1% NEAA, 1% PS, and 2.5 pg/mL trypsin was used as the testing medium for MDCK cells.

In 384-well plates, MDCK cells were seeded at 2,000 cells per well and cultured at 37° C. and 5% $CO_2$ overnight. Next day, each of the 2-drug combination pairs was tested using a checkboard cross pattern of seven drug concentrations of each compound, including each compound alone, in triplicate plates. Pimodivir (VX-787) was evaluated in parallel as a control compound. The compounds (in DMSO) were plated with the Tecan HP D300 Digital Dispenser. Virus (2 $TCID_{90}$/well) was then added. Test concentrations of the compounds were 0.125, 0.25, 0.5, 1, 2, 4 and 8x $EC_{50}$ values. The compound combinations are listed in Table 4. The final concentration of DMSO (Sigma 34869) in the cell culture medium was 0.5%. The resulting cultures were incubated at 37° C. and 5% $CO_2$ for additional 5 days until virus infection in the virus control displayed significant CPE (as assessed by reduction in viable cell number). To assess cell viability, CCK-8 kit solution (one-bottle colorimetric system, Biolite 35004) was then added to each well and the cells were incubated at 37° C. for 3 hours. Absorbance (460 nm) was measured using a SpectraMax 340PC384 plate reader (Molecular Devices).

Antiviral activity and cytotoxicity of the compound combinations were expressed as % Inhibition and % Viability, respectively, and calculated with the equations below:

Inhibition (%)=(Raw $data_{cpd}$–$Average_{VC}$)/($Average_{CC}$–$Average_{VC}$)*100

Viability (%) =(Raw $data_{cpd}$–$Average_{MC}$)/($Average_{CC}$–$Average_{MC}$)*100

Raw $data_{cpd}$ represents the absorbance values of the compound-treated wells; $Average_{VC}$, $Average_{CC}$ and $Average_{MC}$ are the average absorbance values of the virus control (VC; cells infected with virus, without compound), cell control (CC; cells without virus or compound) and medium control (MC, medium only), respectively. The combination indices were calculated using the MacSynergy™ II software (Prichard and Shipman, 1990). Synergy volume plots (95%) were then calculated. A positive combination index value indicates synergism, and a negative combination index value indicates antagonism.

As shown in the tables below, 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid showed strong synergistic effect with influenza antiviral drugs including baloxavir (free hydroxyl form of the baloxavir marboxil prodrug), oseltamivir acid, and favipiravir in influenza antiviral CPE assays against I FV A/PR/8/34 (H1N 1).

| Combination | Compound | Synergy volume (95%) | Antagonism volume (95%) | Combination effect |
|---|---|---|---|---|
| 1 | Baloxavir | 285.84 | −12.28 | Strong synergism |
| 2 | Oseltamivir acid | 269.37 | −9.19 | Strong synergism |
| 3 | Favipiravir | 413.85 | −3.15 | Strong synergism |

An absolute combination index value of <25 (i.e., synergy volume 95%) indicates an additive effect. An absolute combination index value of 25-50 indicates slight synergism or antagonism. An absolute combination index value of 50-100 indicates moderate synergism or antagonism. An absolute combination index value of >100 indicates strong synergism or antagonism.

Figure 2:
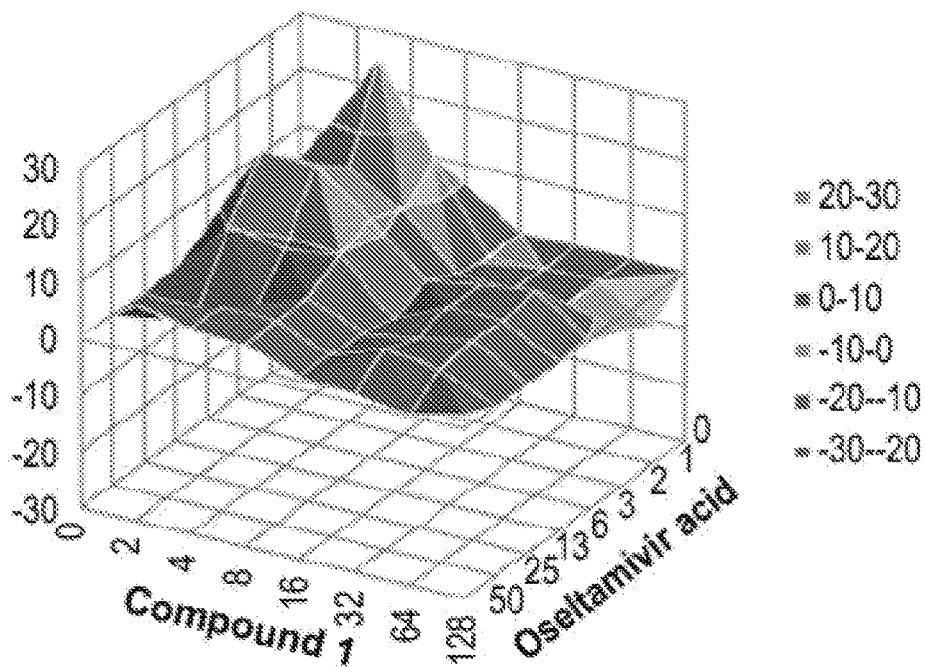
Figure 3:
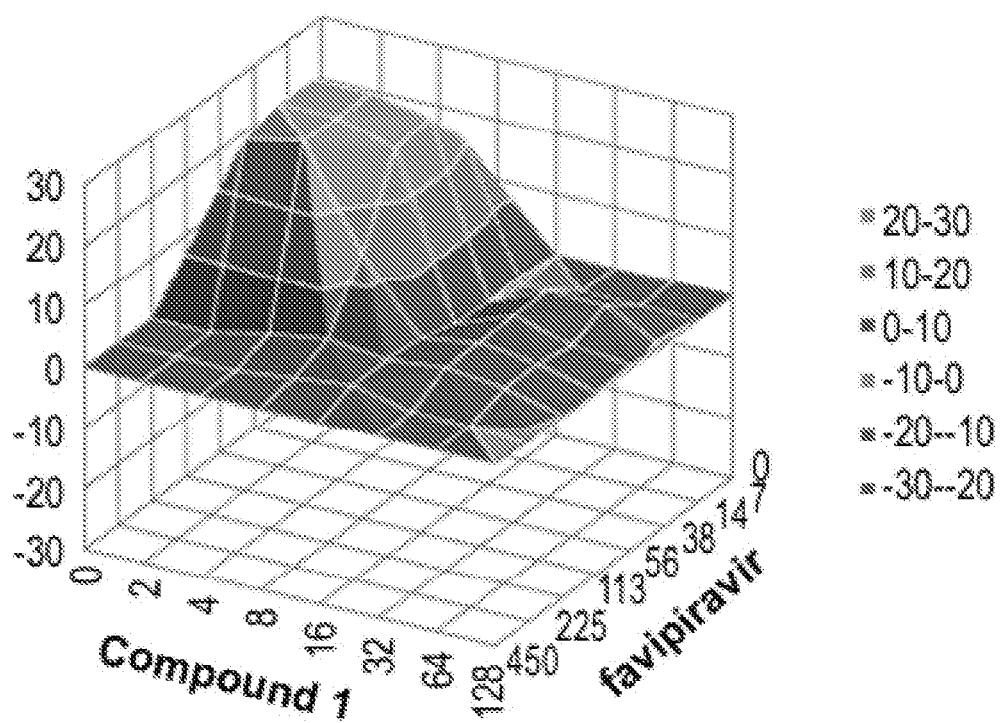

FIGS. 1-3 provide visual representations of the respective calculated plots for the three test combinations.

These same three combinations of Compound 1 with baloxavir (free hydroxyl form of the baloxavir marboxil prodrug), oseltamivir acid, and favipiravir also exhibit antiviral activity against influenza B.

What is claimed is:

1. A method of treating influenza virus infection or reducing influenza virus replication in a subject in need thereof comprising administering to the subject a therapeutically effective amount of (1) 3-(2-(5-chloro-1 H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof, and (2) a second antiviral agent selected from the group consisting of baloxavir marboxil, baloxavir, oseltamivir, oseltamivir acid, and favipiravir, or a pharmaceutically acceptable salt or solvate thereof.

2. The method of any one of claim 1, wherein the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof is administered before the second antiviral agent.

3. The method of any one of claim 1, wherein the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof is administered after the second antiviral agent.

4. The method of any one of claim 1, wherein the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and the second antiviral agent are administered at the same time.

5. The method of claim 4, wherein the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and the second antiviral agent are co-formulated.

6. The method of claim 4, wherein the 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and the second antiviral agent are in separate formulations.

7. The method of claim 1, wherein the second antiviral agent is oseltamivir, oseltamivir acid, or a pharmaceutically acceptable salt or solvate thereof.

8. The method of claim 1, wherein the second antiviral agent is baloxavir marboxil, baloxavir, or a pharmaceutically acceptable salt or solvate thereof.

9. The method of claim 1, wherein the second antiviral agent is favipiravir, or a pharmaceutically acceptable salt or solvate thereof.

10. A method for treating influenza virus infection or replication, comprising administering to a human patient having or at risk of influenza infection 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid, or a pharmaceutically acceptable salt or solvate thereof in a dose of about 10-1,000 mg/kg and a therapeutically effective amount of a second antiviral agent selected from the group consisting of baloxavir marboxil, baloxavir, oseltamivir, oseltamivir acid, and favipiravir, or a pharmaceutically acceptable salt or solvate thereof.

11. The method of claim 10, wherein the second antiviral agent is oseltamivir, oseltamivir acid, or a pharmaceutically acceptable salt or solvate thereof.

12. The method of claim 10, wherein the second antiviral agent is baloxavir marboxil, baloxavir, or a pharmaceutically acceptable salt or solvate thereof.

13. The method of claim 10, wherein the second antiviral agent is favipiravir, or a pharmaceutically acceptable salt or solvate thereof.

14. A combination comprising 3-(2-(5-chloro-1H-pyrrolo[2,3-b]pyridin-3-yl)-5-fluoro-7H-pyrrolo[2,3-d]pyrimidin-7-yl)bicyclo[2.2.2]octane-2-carboxylic acid or a pharmaceutically acceptable salt or solvate thereof and a second antiviral agent selected from the group consisting of baloxavir marboxil, baloxavir, oseltamivir, oseltamivir acid, and favipiravir, or a pharmaceutically acceptable salt or solvate thereof.

15. The combination of claim 14, wherein the second antiviral agent is oseltamivir, oseltamivir acid, or a pharmaceutically acceptable salt or solvate thereof.

16. The combination of claim 14, wherein the second antiviral agent is baloxavir marboxil, baloxavir, or a pharmaceutically acceptable salt or solvate thereof.

17. The combination of claim 14, wherein the second antiviral agent is favipiravir, or a pharmaceutically acceptable salt or solvate thereof.

18. A method for treating an Influenza A or Influenza B infection in a host, reducing endonuclease activity of influenza polymerase in an influenza A or B virus in a host, or reducing influenza virus replication in a host, comprising administering to the host a therapeutic amount of the combination of claim 14.

19. The method of claim 18, further comprising contacting the influenza virus with or administering to the host a therapeutically effective amount of a third antiviral agent.

20. The method of claim 19, further comprising administering to the host an influenza vaccine before, after, or concurrently with the combination.

* * * * *